United States Patent [19]

Ingle et al.

[11] Patent Number: 6,081,749
[45] Date of Patent: Jun. 27, 2000

[54] NONINVASIVE DEVICES, METHODS, AND SYSTEMS FOR SHRINKING OF TISSUES

[75] Inventors: Frank Ingle, Palo Alto; Garry Carter, Pleasanton, both of Calif.

[73] Assignee: SURx, Inc., Pleasanton, Calif.

[21] Appl. No.: 08/910,371

[22] Filed: Aug. 13, 1997

[51] Int. Cl.$^7$ ............................................. A61B 17/39
[52] U.S. Cl. ...................... 607/101; 607/102; 607/105; 606/41
[58] Field of Search .................... 607/101, 102, 607/104, 105; 606/41

[56] References Cited

U.S. PATENT DOCUMENTS

| | | |
|---|---|---|
| 373,399 | 11/1887 | Hamilton . |
| 728,883 | 5/1903 | Downes . |
| 3,575,158 | 4/1971 | Summers ................................... 128/1 |
| 3,749,098 | 7/1973 | De Bennetot ........................... 128/346 |
| 3,924,631 | 12/1975 | Mancusi, Jr. ............................. 128/346 |
| 3,926,175 | 12/1975 | Allen et al. ................................. 128/1 |
| 3,939,821 | 2/1976 | Roth ........................................... 128/1 |
| 4,311,145 | 1/1982 | Esty et al. .......................... 128/303.17 |
| 4,409,453 | 10/1983 | Smith ................................... 219/10.55 |
| 4,453,536 | 6/1984 | Abild ......................................... 128/1 |
| 4,679,561 | 7/1987 | Doss ....................................... 128/422 |
| 4,686,962 | 8/1987 | Haber ......................................... 128/1 |
| 4,765,331 | 8/1988 | Petruzzi et al. .................... 128/303.14 |
| 4,773,393 | 9/1988 | Haber et al. .............................. 600/30 |
| 4,776,344 | 10/1988 | Shirasaki et al. ....................... 128/681 |
| 4,802,479 | 2/1989 | Haber et al. ............................ 128/344 |
| 4,807,620 | 2/1989 | Strul et al. ............................ 128/303.1 |
| 4,832,680 | 5/1989 | Haber et al. .............................. 600/31 |
| 4,994,019 | 2/1991 | Fernandez et al. ....................... 600/30 |

(List continued on next page.)

FOREIGN PATENT DOCUMENTS

| | | | |
|---|---|---|---|
| WO 93/07815 | 4/1993 | WIPO ............................ A61B 17/12 |
| WO 96/00041 | 1/1996 | WIPO ............................ A61B 17/39 |
| WO 96/00042 | 1/1996 | WIPO ............................ A61B 17/39 |
| WO 96/34568 | 11/1996 | WIPO . |
| WO 97/15238 | 5/1997 | WIPO ............................ A61B 17/39 |
| WO 97/20510 | 6/1997 | WIPO ............................ A61B 17/39 |
| WO 97/24992 | 7/1997 | WIPO . |
| WO 97/32532 | 9/1997 | WIPO ............................ A61B 17/39 |
| WO 97/39688 | 10/1997 | WIPO ......................... A61B 17/068 |
| WO 97/43970 | 11/1997 | WIPO ............................ A61B 17/39 |
| WO 97/43971 | 11/1997 | WIPO ............................ A61B 17/39 |
| WO 98/05286 | 2/1998 | WIPO . |
| WO 98/05380 | 2/1998 | WIPO . |
| WO 98/07468 | 2/1998 | WIPO ............................. A61N 1/40 |
| WO 98/38936 | 9/1998 | WIPO ............................ A61B 17/39 |
| WO 99/16502 | 4/1999 | WIPO . |

OTHER PUBLICATIONS

Hayes et al., "Prediction of transient temperature fields and cumulative tissue destruction for radio frequency heating of a tumor" Med. Phys. (1985) 12(6):684–692.

Hayes et al., "Prediction of Transient Temperature Fields and Cumulative Tissue Destruction for Radio Frequency Heating of a Tumor," *Medical Physics*, University of Texas, Austin, Texas; 12(6):1985.

*Primary Examiner*—Robert L. Nasser
*Attorney, Agent, or Firm*—Townsend Townsend & Crew LLP; Mark D. Barrish, Esq.

[57] ABSTRACT

The invention provides improved devices, methods, and systems for shrinking of collagenated tissues, particularly for treating urinary incontinence in a noninvasive manner by directing energy to a patient's own support tissues. This energy gently heats fascia and other collagenated support tissues, causing them to contract. The energy will preferably be applied between a pair of large plate electrodes having cooled flat electrode surfaces. Such cooled plate electrodes are capable of directing electrical energy through an intermediate tissue and into fascia while the cooled electrode surface prevents injury to the intermediate tissue. Ideally, the plate electrode comprises an electrode array including discrete electrode surface segments so that the current flux can be varied to selectively target the fascia.

27 Claims, 8 Drawing Sheets

U.S. PATENT DOCUMENTS

| | | | |
|---|---|---|---|
| 5,012,822 | 5/1991 | Schwarz | 128/885 |
| 5,035,696 | 7/1991 | Rydell | 606/47 |
| 5,057,106 | 10/1991 | Kasevich et al. | 606/33 |
| 5,098,429 | 3/1992 | Sterzer | 606/28 |
| 5,140,999 | 8/1992 | Ardito | 128/885 |
| 5,190,517 | 3/1993 | Zieve et al. | 604/22 |
| 5,201,732 | 4/1993 | Parins et al. | 606/47 |
| 5,234,409 | 8/1993 | Goldberg et al. | 604/96 |
| 5,256,133 | 10/1993 | Spitz | 600/29 |
| 5,281,217 | 1/1994 | Edwards et al. | 606/41 |
| 5,281,218 | 1/1994 | Imran | 606/41 |
| 5,282,799 | 2/1994 | Rydell | 606/48 |
| 5,293,869 | 3/1994 | Edwards et al. | 128/642 |
| 5,304,123 | 4/1994 | Atala et al. | 604/54 |
| 5,309,910 | 5/1994 | Edwards et al. | 128/642 |
| 5,314,465 | 5/1994 | Maurer et al. | 607/138 |
| 5,314,466 | 5/1994 | Stern et al. | 607/156 |
| 5,366,490 | 11/1994 | Edwards et al. | 607/99 |
| 5,370,675 | 12/1994 | Edwards et al. | 607/101 |
| 5,370,677 | 12/1994 | Rudie et al. | 607/101 |
| 5,370,678 | 12/1994 | Edwards et al. | 607/101 |
| 5,376,064 | 12/1994 | Cerny | 600/30 |
| 5,385,544 | 1/1995 | Edwards et al. | 604/22 |
| 5,403,312 | 4/1995 | Yates et al. | 606/50 |
| 5,405,346 | 4/1995 | Grundy et al. | 606/41 |
| 5,411,475 | 5/1995 | Atala et al. | 604/54 |
| 5,423,811 | 6/1995 | Imran et al. | 606/41 |
| 5,431,649 | 7/1995 | Mulier et al. | 606/41 |
| 5,437,603 | 8/1995 | Cerny et al. | 600/29 |
| 5,437,664 | 8/1995 | Cohen et al. | 606/42 |
| 5,447,529 | 9/1995 | Marchlinski et al. | 607/99 |
| 5,454,809 | 10/1995 | Janssen | 606/41 |
| 5,458,596 | 10/1995 | Lax et al. | 606/31 |
| 5,462,545 | 10/1995 | Wang et al. | 606/41 |
| 5,496,312 | 3/1996 | Klicek | 606/34 |
| 5,514,130 | 5/1996 | Baker | 606/41 |
| 5,536,267 | 7/1996 | Edwards et al. | 606/41 |
| 5,540,655 | 7/1996 | Edwards et al. | 604/22 |
| 5,540,679 | 7/1996 | Fram et al. | 607/102 |
| 5,542,916 | 8/1996 | Hirsch et al. | 604/22 |
| 5,549,644 | 8/1996 | Lundquist et al. | 604/22 |
| 5,554,110 | 9/1996 | Edwards et al. | 604/22 |
| 5,569,242 | 10/1996 | Lax et al. | 606/42 |
| 5,588,960 | 12/1996 | Edwards et al. | 604/20 |
| 5,591,125 | 1/1997 | Edwards et al. | 604/22 |
| 5,609,598 | 3/1997 | Laufer et al. | 606/142 |
| 5,628,770 | 5/1997 | Thome et al. | 607/101 |
| 5,667,488 | 9/1997 | Lundquist et al. | 604/22 |
| 5,673,695 | 10/1997 | McGee et al. | 607/101 |
| 5,687,723 | 11/1997 | Avitall | 607/101 |
| 5,697,281 | 12/1997 | Eggers et al. | 604/114 |
| 5,697,536 | 12/1997 | Eggers et al. | 604/114 |
| 5,697,882 | 12/1997 | Eggers et al. | 604/114 |
| 5,697,909 | 12/1997 | Eggers et al. | 606/114 |
| 5,755,753 | 5/1998 | Knowlton . | |
| 5,769,879 | 6/1998 | Richards et al. | 607/101 |
| 5,792,140 | 8/1998 | Tu et al. | 607/101 |
| 5,810,847 | 9/1998 | Laufer et al. | 606/142 |
| 5,871,524 | 2/1999 | Knowlton . | |
| 5,895,417 | 4/1999 | Pomeranz et al. | 607/101 |
| 5,919,219 | 7/1999 | Knowlton . | |
| 5,948,011 | 9/1999 | Knowlton . | |
| 6,015,407 | 1/2000 | Rieb et al. | 607/101 |

NONINVASIVE DEVICES, METHODS, AND SYSTEMS FOR SHRINKING OF TISSUES

CROSS REFERENCE TO RELATED APPLICATIONS

This application is related to U.S. patent applications Ser. No.08/910,370, Serial No. 08/910,775, and Serial No. 08/910,369, all filed concurrently herewith, the full disclosures of which are incorporated herein by reference.

BACKGROUND OF THE INVENTION

1. Field of the Invention

The present invention generally relates to medical devices, methods, and systems. More specifically, the present invention provides techniques for selectively heating and shrinking tissues, particularly for the noninvasive treatment of urinary incontinence and hernias, for cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such noninterventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods which made use of the existing support structures of the body, rather than depending on the specific length of an artificial support structure.

2. Description of the Background Art

U.S. Pat. No. 5,423,811 describes a method for RF ablation using a cooled electrode. U.S. Pat. Nos. 5,458,596 and 5,569,242 describe methods and an apparatus for controlled contraction of soft tissue. An RF apparatus for controlled depth ablation of soft tissue is described in U.S. Pat. No. 5,514,130.

U.S. Pat. No. 4,679,561 describes an implantable apparatus for localized heating of tissue, while U.S. Pat. No. 4,765,331 describes an electrosurgical device with a treatment arc of less than 360 degrees. An impedance and temperature generator control is described in U.S. Pat. No. 5,496,312. Bipolar surgical devices are described in U.S. Pat. Nos. 5,282,799, 5,201,732, and 728,883.

SUMMARY OF THE INVENTION

The present invention provides devices, methods, and systems for shrinking of collagenated tissues, particularly for treating urinary incontinence in a noninvasive manner. In contrast to prior art techniques, the present invention does not rely on implantation of balloons or other materials, nor does it rely on suturing, cutting, or other direct surgical modifications to the natural support tissues of the body. Instead, the present invention directs energy to a patient's own support tissues. This energy gently heats fascia and other collagenated support tissues, causing them to contract without substantial necrosis of adjacent tissues. The energy will preferably be applied through a large, cooled electrode having a substantially flat electrode surface. Such a cooled plate electrode is capable of directing electrical energy through an intermediate tissue and into fascia, while the cooled electrode surface prevents injury to the intermediate tissue. Ideally, the plate electrode comprises an electrode array which includes several discrete electrode surface segments so that the current flux can be varied to selectively target and evenly heat the fascia. In some embodiments, the tissue is heated between a pair of parallel cooled electrode surfaces, the parallel surfaces optionally being planar, cylindrical, spherical, or the like.

In a first aspect, the present invention provides a probe for heating a target tissue of a patient body through an intermediate tissue. The probe comprises a probe body supporting an electrode array. The electrode array includes a plurality of electrode surface segments. The electrode surface segments are simultaneously engagable against the intermediate tissue, and a cooling system is coupled to the probe for cooling the electrode surface segments. A control system is also coupled to the electrode surface segments. The control system is adapted to selectively energize the electrode surface segments so as to heat the target tissue to a treatment temperature while the cooling system maintains the intermediate tissue (which is disposed between the electrode array and the target zone) at or below a maximum safe tissue temperature.

In another aspect, the present invention provides a method for therapeutically heating a target zone of a tissue within a patient body. The method comprises engaging a probe against the tissue. The probe has a plurality of electrode surface segments, and the tissue is cooled adjacent the probe by the electrode surface segments. An electrical current flux is directed from the electrode surface segments, through the cooled tissue, and into the target zone by selectively energizing the electrode surface segments so that the current flux substantially evenly heats the target zone.

BRIEF DESCRIPTION OF THE DRAWINGS

FIGS. 3–3E graphically illustrate a method for heating a target tissue between cooled electrodes, wherein the electrode surfaces cool the tissue before, during, and after radiofrequency energy is applied.

DETAILED DESCRIPTION OF THE SPECIFIC EMBODIMENTS

The present invention optionally relies on inducing controlled shrinkage or contraction of a support tissue of the body, typically being a collagenated tissue such as fascia, ligament, or the like. For treatment of urinary incontinence, the tissue structure will be one that is responsible in some manner for control of urination, or for supporting a such a tissue. Exemplary tissue structures include the urethral wall, the bladder neck, the bladder, the urethra, bladder suspension ligaments, the sphincter, pelvic ligaments, pelvic floor muscles, fascia, and the like. Treatment of other conditions may be effected by selective shrinking of a wide variety of other tissues, including (but not limited to) the diaphragm, the abdominal wall, the fascia and ligaments of the joints, and the like. Related devices, methods, and system are also described in co-pending U.S. patent application Ser. No. 08/910,370, filed herewith, the full disclosure of which is incorporated herein by reference.

Tissue contraction results from controlled heating of the tissue by affecting the collagen molecules of the tissue. Contraction occurs as a result of heat-induced uncoiling and repositioning of the collagen β-pleated structure. By maintaining the times and temperatures set forth below, significant tissue contraction can be achieved without substantial collateral tissue necrosis.

The temperature of the target tissue structure will generally be raised to a value in the range from about 60° C. to 110° C., often being in the range from about 60° C. to 80° C., and will generally effect a shrinkage of the target tissue in at least one dimension of between about 20 and 50 percent. In many embodiments, heating energy will be applied for a period of from 30 seconds to 5 minutes. These heating times will vary with separation between the parallel plate electrodes, with a heat time of about 5 minutes often being appropriate for an electrode separation of about 4 cm. Shorter heat times may be used with smaller electrode separation distances.

The rise in temperature may be quite fast, although there will often be advantages in heating tissues more slowly, as this will allow more heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy. Fortunately, fascia and other support tissues often have less bloodflow than adjacent tissues and organs; this may help enhance the heating of fascia and minimize necrosis of the surrounding structures.

The total amount of energy delivered will depend in part on which tissue structure is being treated, how much tissue is disposed between the target tissue and the heating element, and the specific temperature and time selected for the protocol. The power delivered will often be in the range from 10 W to 100 W, usually being about 20 W. The temperature will usually not drop instantaneously when the heating energy stops, so that the tissue may remain at or near the therapy temperature for a time from about 10 seconds to about 2 minutes, and will often cool gradually back to body temperature.

While the remaining description is generally directed at devices and methods for treatment of urinary stress incontinence of a female patient, it will be appreciated that the present invention will find many other applications for selectively directing therapeutic heating energy into the tissues of a patient body for shrinking of tissues, for ablation of tissues and tumors, and the like.

Figure 1:
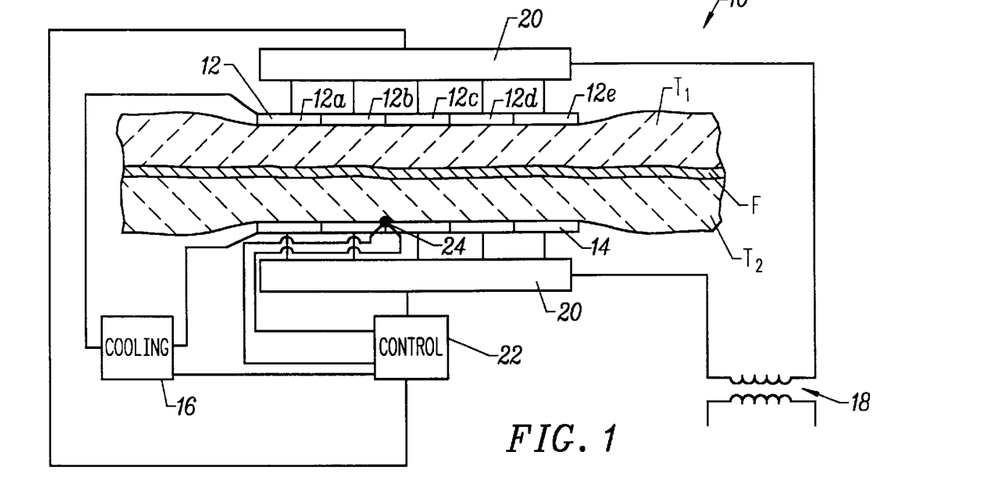
FIG. 1 is a schematic illustration of a system for heating and shrinking fascia disposed between adjacent tissue layers by heating the fascia between a pair of large, cooled, flat electrode arrays, according to the principles of the present invention.

FIG. 1 schematically illustrates a system 10 for shrinking a fascia F disposed between first and second adjacent tissues T1, T2. System 10 includes a pair of electrodes 12, 14 having large, substantially planar tissue engaging surfaces. Electrodes 12, 14 are aligned substantially parallel to each other with the fascia (and adjacent tissues) disposed therebetween.

The surfaces of electrodes 12, 14 which engage the tissue are cooled by a cooling system 16. The cooling system will typically include a conduit through the electrode for the circulation of a cooling fluid, but may optionally rely on thermoelectric cooling or the like. The temperature of the electrode surface may be regulated by varying the temperature or flow rate of the cooling fluid. Cooling may be provided through the use of an ice bath, by endothermic chemical reactions, by standard surgical room refrigeration mechanisms, or the like. Ideally, the cooling system cools an area which extends beyond the energized electrode surfaces to prevent any hot spots adjacent the tissue surface, and to maximize the heat removal from the tissue without having to resort to freezing the tissue.

Each of the electrodes is separated into a plurality of electrode segments. For example, the electrode includes electrode segments 12a, 12b, 12c, 12d, and 12e, each of which is electrically isolated from the others. This allows the electrode segments to be individually energized. Electrodes 12, 14 are energized by a radiofrequency (RF) power source 18. Multiplexers 20 individually energize each electrode segment, typically varying the power or time each segment is energized to more nearly uniformly heat fascia F. A controller 22 will typically include a computer program which directs the application of cooling flow and RF power through electrodes 12, 14, ideally based at least in part on a temperature signal sensed by a temperature sensor 24. Temperature sensor 24 may sense the temperature of the tissue at the tissue/electrode interface, or may alternatively sense the temperature of the fascia itself.

Figure 2:
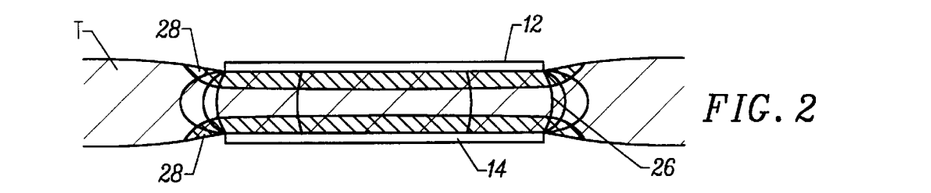
FIG. 2 schematically illustrates the even heating provided by a current flux between the large, cooled, flat electrode surfaces of the system of FIG. 1.

The use of large cooled plate electrodes to direct an even electrical current flux can be understood with reference to the simplified cross-sectional illustration of FIG. 2. In this example, RF power is applied uniformly across parallel plate electrodes 12, 14 to produce a current through tissue T. As the electrode surfaces are substantially planar, and as the electrode surfaces are large compared to the separation between the electrodes, a current flux 26 is substantially uniform throughout that portion of the tissue which is disposed between the electrode surfaces. The flow of electrical current through the electrical resistance of the tissue causes the temperature of the tissue through which the current passes to rise. The use of relatively low radiofrequency current, preferably in the range from 100 kHz to 1 MHz, helps to avoid collateral damage to nerve and muscle tissues.

Preliminary work in connection with the present invention has shown that fascia and other collagenated tissues which are heated to a temperature range of between about 60° C. and 110° C., and preferably between about 60° C. and 80° C., will contract. In fact, unstressed fascia will shrink between about 30% and 50% when heated for a very short time, preferably from between about 0.5 seconds to 5 seconds. Such heating can easily be provided by conduction of RF currents through the tissue.

The uniform current flux provided by the large plate electrodes of the present invention will produce a substantially uniform heating of the tissue which passes that current. To selectively target a central portion of the tissue, in other words, to selectively heat a target portion of the tissue separated from electrodes 12, 14, the electrode surfaces are cooled. This cooling maintains a cooled tissue region 28 adjacent each electrode below a maximum safe tissue temperature, typically being below about 45° C. Even though heat generation throughout the gap between the electrodes is uniform, the temperature profile of the tissue between the electrodes can be controlled by removing heat through the electrode surfaces during heating.

Generally, sufficient heating can be provided by a current of between about 0.2 and 2.0 amps, ideally about 1.0 amp, and a maximum voltage of between about 30 and 100 volts rms, ideally being about 60 volts rms. The electrodes will often have a surface area of between about 5.0 and 200 $cm^2$, and the current density in the target tissue will often be between about 1 $mA/cm^2$ and 10 $mA/cm^2$. This will provide a maximum power in the range from about 10 W to about 100 W, often being about 20 watts. Using such low power settings, if either electrode is lifted away from the engaged tissue, there will be no arcing. Instead, the current will simply stop. This highlights the difference between the electrical tissue heating of the present invention and known electrocautery techniques.

The ideal geometry to provide a true one-dimensional temperature distribution would include large parallel plate electrodes having relatively minimal spacing therebetween. As tissues which are easily accessible for such structures are fairly limited, the present invention can also make use of electrode geometries which vary somewhat from this ideal, particularly through the use of array electrodes. In fact, the use of a single array electrode, in combination with a much larger, uncooled electrode pad may heat tissues disposed near the array, as will be described hereinbelow. Nonetheless, uniform heating is generally enhanced by providing electrode structures having tissue engaging surfaces which are as flat and/or as parallel as practical. Preferably, the parallel electrode surfaces will be separated by between about 1/3 and 1.0 times the width of the electrode surfaces (or of the smaller surface, if they are different).

Figure 2A:
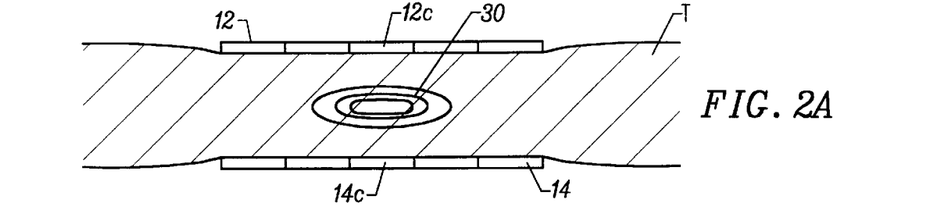
FIGS. 2A–2F schematically illustrate structures and methods for selectively energizing the electrode surface segments of the large, flat electrode arrays of the system of FIG. 1 to tailor the current flux throughout a target zone.
Figure 2B:
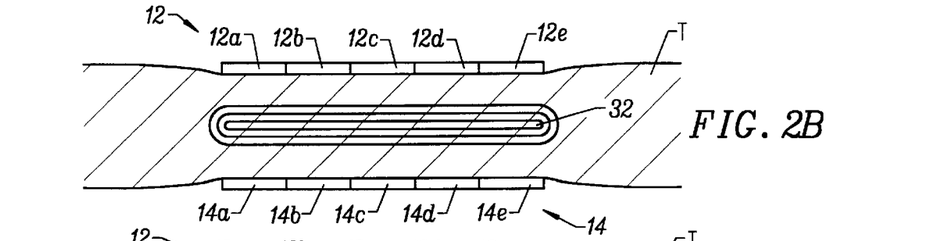

The use of an array electrode having multiple electrode segments can be understood with reference to FIGS. 2A–2D. FIG. 2A schematically illustrates the shape of a target zone which is heated by selectively energizing only electrode segments 12c and 14c of cooled electrodes 12 and 14. Once again, it should be understood that the temperature of target zone 32 (here illustrated schematically with isotemperature contour lines 30) is the result of uniform heating between the energized electrode segments, in combination with cooling of tissue T by the electrode surfaces. To expand the heated area laterally between the electrodes, electrode segments 12a, 12b, 12c . . . , and 14a, 14b, 14c . . . , can be energized, thereby heating an entire target zone 32 extending throughout tissue T between the electrodes.

Figure 2C:
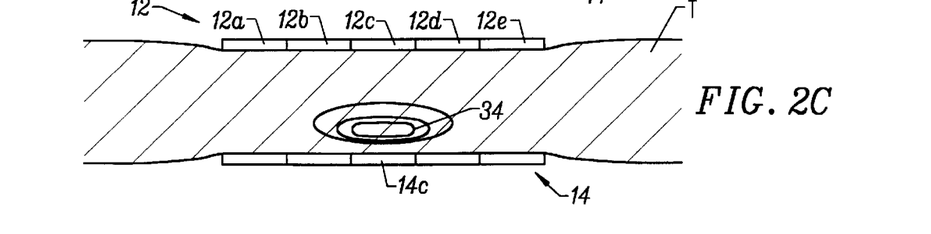

The use of array electrodes provides still further flexibility regarding the selective targeting of tissues between electrodes 12 and 14. As illustrated in FIG. 2C, selectively energizing a relatively large effective electrode surface by driving electrodes segments 12a, 12b, 12c, 12d, and 12e results in a low current flux which is widely disbursed throughout the tissue T engaged by electrode 12. By driving this same current through a relatively small effective electrode surface using only a single electrode surface segment 14c produces an offset target zone 34 which is much closer to electrode 14 than to electrode 12.

Figure 2D:
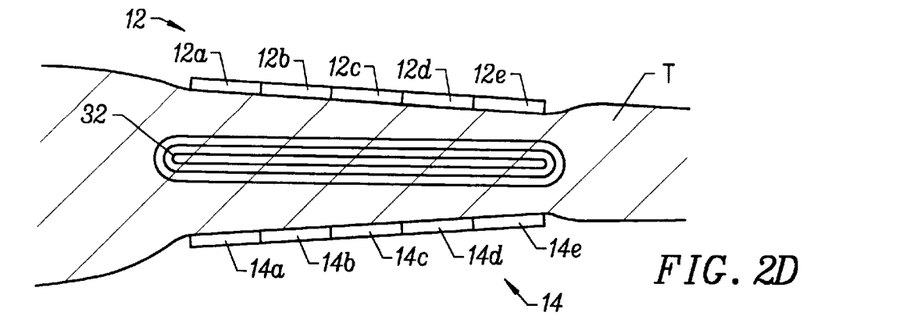
Figure 2E:
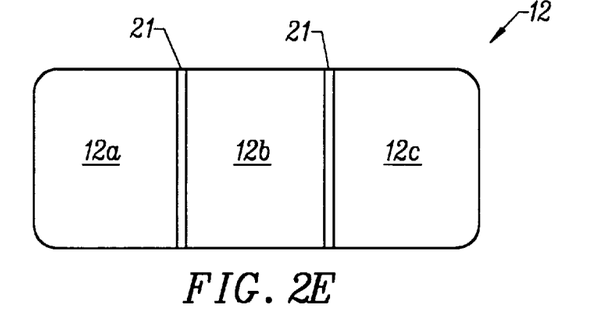

To compensate for electrode structures which are not exactly parallel, varying amounts of electrical current can be provided to the electrode segments. For example, a fairly uniform target zone 32 may be heated between angled electrodes by driving more current through relatively widely spaced electrode segments 12a, 14a, and driving less current through more tightly spaced electrode segments 12e, 14e, as illustrated in FIG. 2D. It should be understood that these selective targeting mechanisms may be combined to target fascia and other tissues which are near one slanted electrode, or to selectively target only a portion of the tissues disposed between relatively large electrode arrays.

Figure 2F:
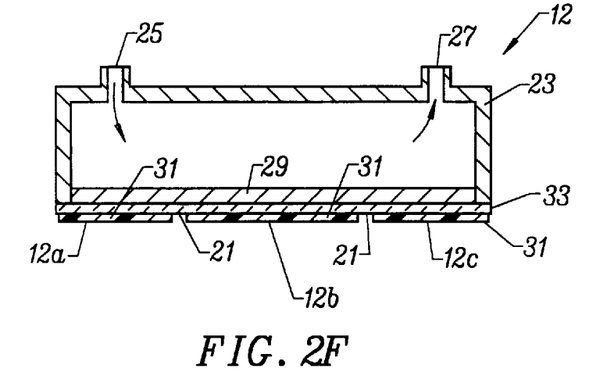

An exemplary structure for segmented, cooled electrode 12 is schematically illustrated in FIG. 2F. Electrode 12 here comprises three electrode surface segments 12a, 12b, and 12c separated by insulating spaces 21. A plastic housing 23 defines a flow path between a cooling inflow port 25 and a cooling outflow port 27, while heat transfer between the cooling fluid and the electrode surface is enhanced by a thermally conductive front plate 29. Front plate 29 generally comprises a thermally conductive metal such as aluminum. Electrode surface segments 12a, 12b, and 12c may comprise surfaces of separated segments 31 of aluminum foil. Segments 31 may be electrically isolated by a mylar insulation sheet 33 disposed between the segments and front plate 29.

The array electrode structures of the present invention will generally include a series of conductive surface segments which are aligned to define a substantially flat electrode surface. The electrode surface segments are separated by an electrically insulating material, with the insulation being much smaller in surface area than the conductive segments. Typically, there will be between 1.0 and 8.0 electrode segments, which are separated by a distance of between about 0.25 mm and 1.0 mm.

It should also be understood that while the electrode arrays of the present invention are generally herein described with reference to a linear array geometry, the present invention also encompasses electrodes which are segmented into two-dimensional arrays. Where opposed sides of the tissue are accessible for relatively large array structures, such as along the exposed skin, or near the major cavities and orifices of the body, the electrode surfaces will preferably be separated by a gap which is less than a width (and length) of the electrodes.

In some embodiments, one electrode structure may be disposed within a large body cavity such as the rectum or vagina, while the other is placed in an adjacent cavity, or on the skin so that the region to be treated is between the electrode surfaces. In other embodiments, one or both electrodes may be inserted and positioned laparoscopically. It will often be desirable to clamp the tissue tightly between the electrodes to minimize the gap therebetween, and to promote efficient coupling of the electrode to the tissue.

Figures 3, 3A:
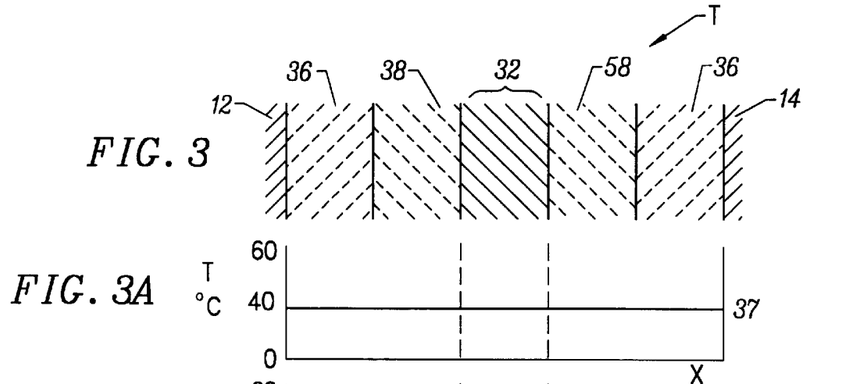
Figure 3B:
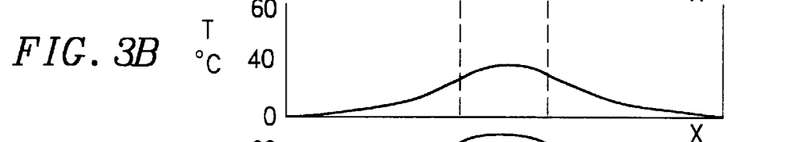
Figure 3C:
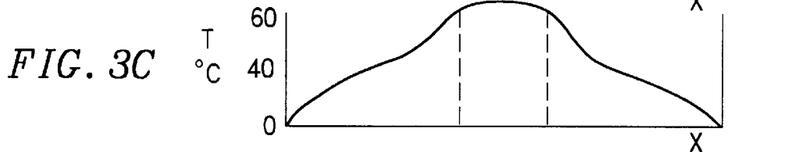
Figure 3D:
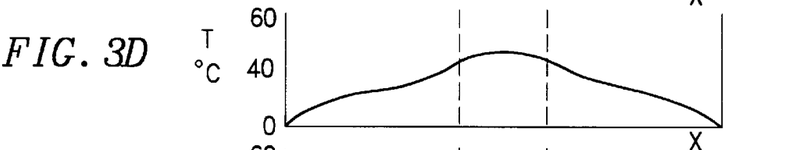
Figure 3E:
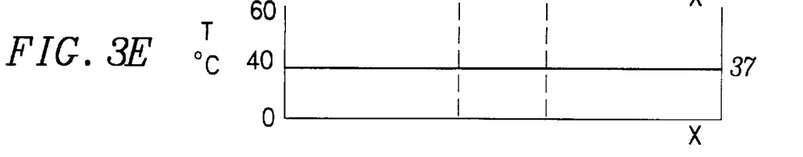

As can be understood with reference to FIGS. 3–3E, the tissue will preferably be cooled before and after energizing of the electrodes. FIG. 3 illustrates three distinct regions of tissue T disposed between electrodes 12 and 14. Target zone 32 will typically comprise fascia or some other collagenated tissue, while the surfaces of the electrodes engage an intermediate tissue 36 disposed on either side of the fascia.

It will generally be desirable to maintain the temperature of intermediate tissue 36 below a maximum safe tissue temperature to prevent injury to this intermediate tissue, the maximum safe tissue temperature typically being about 45° C. To effect shrinkage of fascia, target zone 32 will typically be heated to a temperature above about 60° C.

There will often be a region of stunned tissue 38 disposed between the safely cooled intermediate tissue 36 and the target zone 32. This stunned tissue will typically be heated in the range from about 45° C. to about 60° C., and may therefore undergo some limited injury during the treatment process. As a result, it is generally desirable to minimize the time this tissue is at an elevated temperature, as well as the amount of stunned tissue.

As illustrated in FIG. 3A, prior to application of cooling or heating energy, the temperature profile of tissue T along an axis X between electrodes 12 and 14 is substantially uniform at body temperature. The tissue will preferably be pre-cooled by the surfaces of electrodes 12, 14, generally using an electrode surface temperature of at or above 0° C. Pre-cooling will substantially decrease the temperature of intermediate tissues 36, and will preferably at least partially decrease the temperature of stunned tissue 38. At least a portion of the target zone remains at or near the initial body temperature, as illustrated in FIG. 3B. Pre-cooling time will often depend on electrode separation and tissue heat diffusity.

Once the tissue has been pre-cooled, the RF current is directed through the tissue between the electrodes to heat the tissue. A temperature sensor can be placed at the center of target zone 3z to help determine when the pre-cooling has been applied for the proper time to initiate RF heating. The current flux applies a fairly uniform heating throughout the tissue between the electrodes, and the electrode surfaces are often cooled throughout the heating process. As target zone 32 has the highest temperature upon initiation of the heating cycle, and as the target zone is farthest from the cooled electrodes, a relatively small amount of heat flows from the target zone into the electrodes, and the target zone is heated to a significantly higher temperature than intermediate tissue 36.

Heat is applied until the target zone is at or above a treatment temperature, typically resulting in a temperature distribution such as that illustrated in FIG. 3C. To minimize collateral damage to the adjacent tissues 36 and stunned tissue 38, the cooling system continues to circulate cold fluid through the electrode, and to remove heat from the tissue, after the heating radiofrequency energy is halted. When substantially the entire tissue is below the maximum safe tissue temperature, cooling can be halted, and the tissue can be allowed to return to standard body temperature, as illustrated in FIG. 3E.

Figure 4:
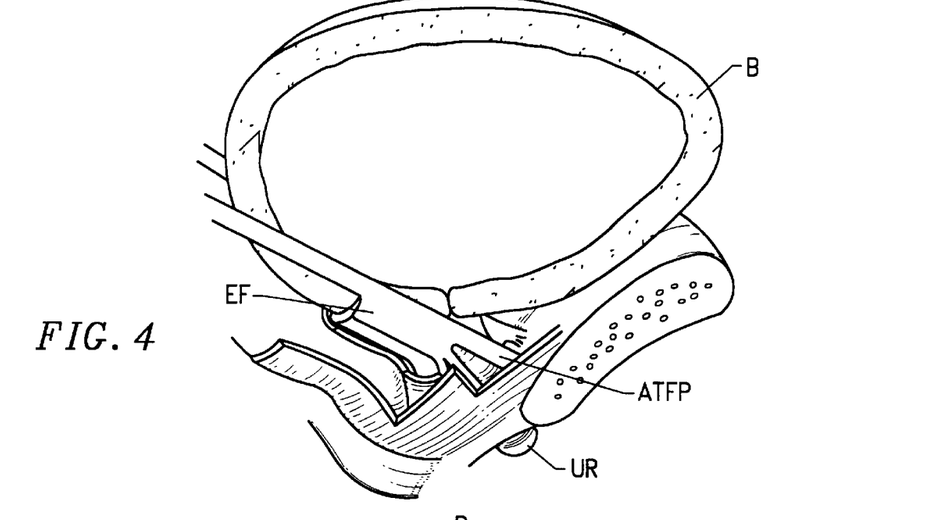
FIG. 4 is a cut-away view illustrating pelvic support structures which can be targeted for non-invasive selective contraction using the methods of the present invention.

The pelvic support tissues which generally maintain the position of the urinary bladder B are illustrated in FIG. 4. Of particular importance for the method of the present invention, endopelvic fascia EF defines a hammock-like structure which extends between the arcus tendineus fascia pelvis ATFP. These latter structures extend between the anterior and posterior portions of the pelvic bone, so that the endopelvic fascia EF largely defines the pelvic floor.

In women with urinary stress incontinence due to bladder neck hypermobility, the bladder has typically dropped between about 1.0 cm and 1.5 cm (or more) below its nominal position. This condition is typically due to weakening of the pelvic support structures, including the endopelvic fascia, the arcus tendineus fascia pelvis, and the surrounding ligaments and muscles, often as the result of bearing children.

When a woman with urinary stress incontinence sneezes, coughs, laughs, or exercises, the abdominal pressure often increases momentarily. Such pressure pulses force the bladder to descend still further, shortening the urethra UR and momentarily opening the urinary sphincter.

Figure 4A:
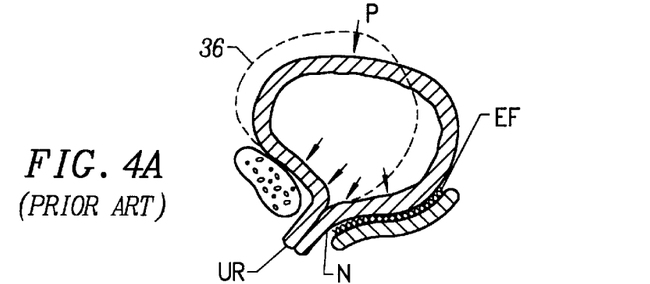
FIGS. 4A–4C illustrate contraction and reinforcing of the pelvic support tissues of FIG. 4 as a therapies for female urinary incontinence.
Figure 4B:
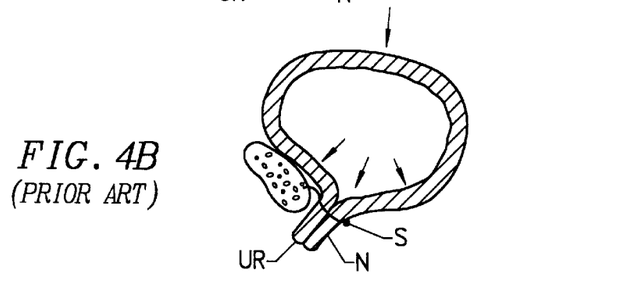
Figure 4C:
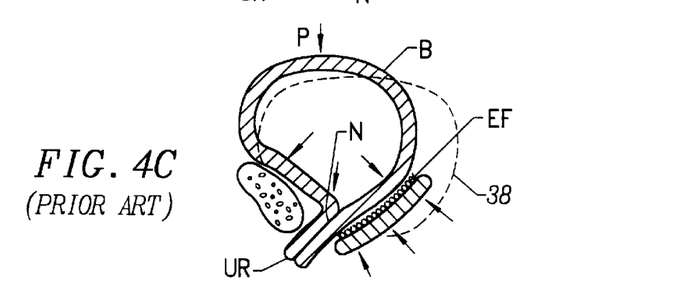

As can be most clearly understood with reference to FIGS. 4A–4C, the present invention generally provides a therapy which applies gentle heating to shrink the length of the support tissues and return bladder B to its nominal position. Advantageously, the bladder is still supported by the fascia, muscles, ligaments, and tendons of the body. Using gentle resistive heating between bipolar electrodes, the endopelvic fascia EF and arcus tendineus fascia pelvis ATFP are controllably contracted to shrink them and re-elevate the bladder toward its original position.

Referring now to FIG. 4A, bladder B can be seen to have dropped from its nominal position (shown in phantom by outline 36). While endopelvic fascia EF still supports bladder B to maintain continence when the patient is at rest, a momentary pressure pulse P opens the bladder neck N, resulting in a release through urethra UR.

A known treatment for urinary stress incontinence relies on sutures S to hold bladder neck N closed so as to prevent inadvertent voiding, as seen in FIG. 4B. Sutures S may be attached to bone anchors affixed to the pubic bone, ligaments higher in the pelvic region, or the like. In any case, loose sutures provide insufficient support of the bladder neck N and fail to overcome urinary stress incontinence, while overtightening of sutures S may make normal urination difficult and/or impossible.

As shown in FIG. 4C, by selectively contracting the natural pelvic support tissues, bladder B can be elevated from its lowered position (shown by lowered outline 38). A pressure pulse P is resisted in part by endopelvic fascia EF, which supports the lower portion of the bladder and helps maintain the bladder neck in a closed configuration. In fact, fine tuning of the support provided by the endopelvic fascia is possible through selective contraction of the anterior portion of the endopelvic fascia to close the bladder neck and raise bladder B upward. Alternatively, lateral repositioning of bladder B to a more forward position may be affected by selectively contracting the dorsal portion of endopelvic fascia EF. Hence, the therapy of the present invention may be tailored to the particular elongation exhibited by a patient's pelvic support tissues.

As is more fully explained in co-pending U.S. patent application Ser. No. 08/910,370 previously incorporated by reference, a wide variety of alternative conditions may also be treated using the methods of the present invention. In particular, selective shrinkage of fascia may effectively treat cystocele, hiatal, and inguinal hernias, and may even be used in cosmetic procedures such as abdominoplasty (through selectively shrinking of the abdominal wall).

Figure 5:
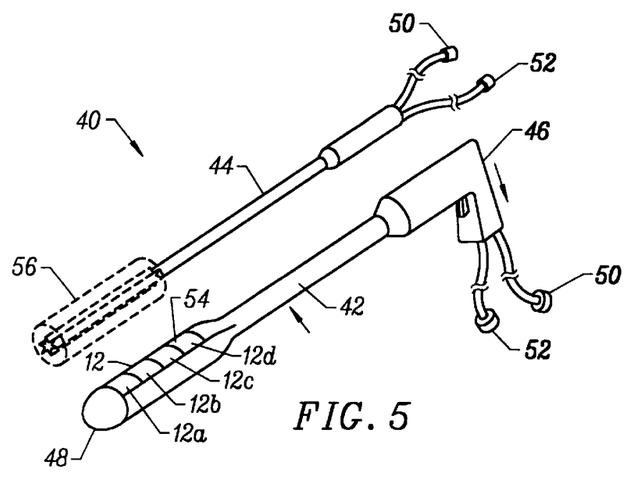
FIG. 5 is a perspective view of a system for treating female urinary incontinence by selectively shrinking the endopelvic fascia, according to the principles of the present invention.

A system for selectively shrinking the endopelvic fascia is illustrated in FIG. 5. System 40 includes a vaginal probe 42 and a bladder probe 44. Vaginal probe 42 has a proximal end 46 and a distal end 48. Electrode 12 (including segments 12a, 12b, 12c, and 12d) is mounted near the distal end of the probe. Vaginal probe 42 will typically have a diameter of between about 2 and 4 cm, and will often have a shaft length of between about 6 and 12 cm. An electrical coupling 50 is couplable to an RF power supply, and optionally to an external control processor. Alternatively, a controller may be integrated into the probe itself. A fluid coupling 52 provides attachment to a cooling fluid system. Cooling fluid may be recycled through the probe, so that more than one fluid couplers may be provided.

The segments of electrode 12 are quite close to each other, and preferably define a substantially flat electrode surface 54. The cooling fluid flows immediately below this surface, the surface material preferably being both thermally and electrically conductive. Ideally, surface 54 is as large as the tissue region to be treated, and a thermocouple or other temperature sensor may be mounted adjacent the surface for engaging the tissue surface and measuring the temperature of the engaged tissue.

Figure 6:
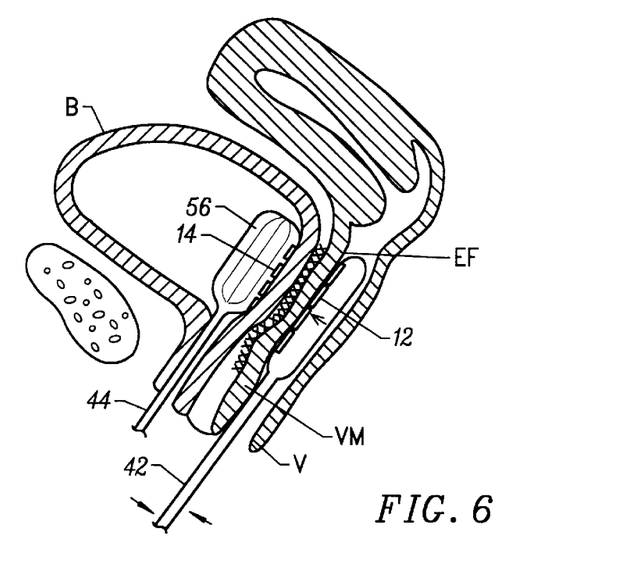
FIG. 6 is a cross-sectional view illustrating a method for using the system of FIG. 5 to treat female urinary incontinence.

Urethral probe 44 includes a balloon 56 supporting a deployable electrode surface. This allows the use of a larger electrode surface than could normally be inserted through the urethra, by expanding the balloon structure within the bladder as illustrated in FIG. 6. Alternatively, a narrower cylindrical electrode might be used which engages the surrounding urethra, the urethral electrode optionally being separated into more than one segment along the length and/or around the circumference of the probe shaft. Radiofrequency current will divert from such a tightly curved surface and heat the nearby tissue. The electrode can again be chilled to protect the urethral lining from thermal damage.

As illustrated in FIG. 6, the endopelvic fascia will preferably be disposed between the electrodes of the urethral probe 44 and vaginal probe 42. Balloon 56 of urethral probe 44 is here illustrated in its expanded configuration, thereby maximizing a surface area of electrode 14, and also minimizing its curvature. Preferably, cooled fluid recirculating through balloon 56 will cool electrode 14, so that cooled electrodes 12, 14 will selectively heat the endopelvic fascia EF without damaging the delicate vaginal mucosa VM or the bladder wall.

Urethral probe 44 and vaginal probe 42 may optionally be coupleable to each other to facilitate aligning the probes on either side of the target tissue, either mechanically or by some remote sensing system. For example, one of the probes may include an ultrasound transducer, thereby facilitating alignment of the electrode surfaces and identification of the target tissue. Alternatively, the proximal ends of the probes may attach together to align the electrodes and/or clamp the target tissue between the probes.

Figure 7:
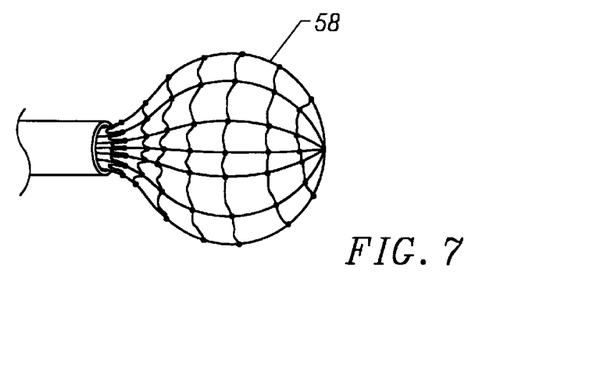
FIG. 7 illustrates an alternative bladder electrode structure for use in the method of FIG. 6.

Referring now to FIG. 7, a mesh electrode 58 may be unfurled within the bladder in place of urethral probe 44. Mesh electrode 58 preferably comprises a highly flexible conductive element, optionally being formed of a shape memory alloy such as Nitinol™. The bladder may be filled with distilled water during the therapy, so that little or no RF current would flow into the bladder wall beyond the contact region between the electrode and the bladder.

Figure 8A:
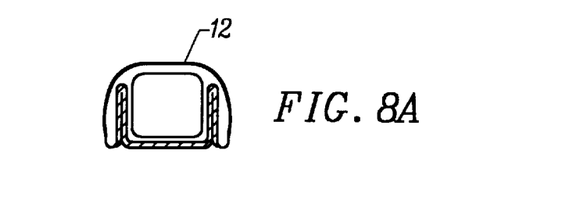
FIGS. 8A and 8B illustrate an alternative vaginal probe having a balloon deployable electrode for use in the method of FIG. 6.
Figures 8B, 9:
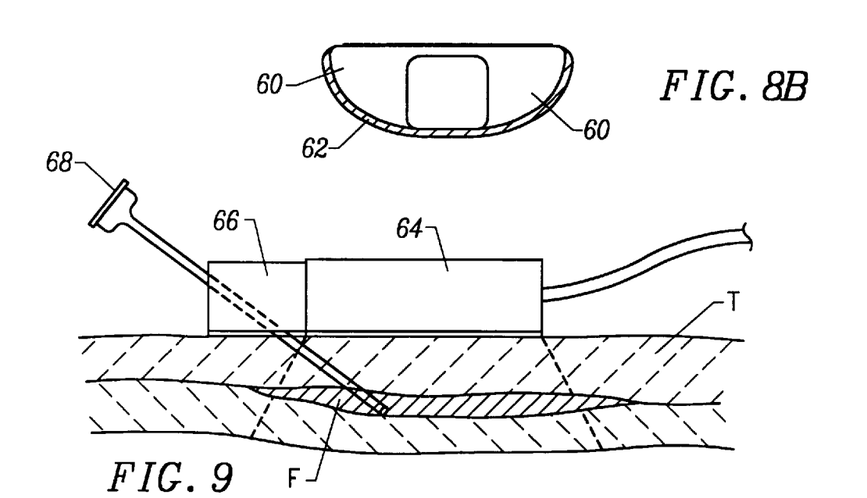
FIG. 9 is a cross-sectional view illustrating a structure and a method for ultrasonically positioning a temperature sensor within a target tissue.

FIGS. 8A and 8B illustrate an optional deployable electrode support structure for use with vaginal probe 42. Electrode 12 can be collapsed into a narrow configuration for insertion and positioning within the vaginal cavity, as illustrated in FIG. 8A. Once electrode 12 is positioned adjacent to the target tissue, electrode 12 can be expanded by inflating lateral balloon 60 so that the deployed electrode assumes a substantially planar configuration. A cooling fluid may be recirculated through lateral balloon 60 to cool the electrode 12, and a thermally insulating layer 62 can help to minimize heat transfer from the adjacent tissues.

Referring now to FIG. 9, the tissue shrinking system of the present invention may also include an ultrasonic transducer 64 for positioning one or both electrodes relative to fascia F. Transducer 64 will preferably include a plastic transducer material such as $PVDF_2$ (polyvinyladine fluoride) or PZT-5A (lead zirconate titanate). Transducer 64 may be incorporated into the probes of the present invention, thereby allowing the relative positions and angle between the electrode surfaces to be measured directly. Alternatively, transducer 64 may be positioned adjacent to fascia F, and a mark may be drawn upon the exposed skin (or other tissue surface) adjacent the fascia for subsequent positioning of a probe. In some embodiments, the treatment probe may include both an ultrasound transducer disposable adjacent the intermediate tissue to facilitate aligning the probe with the target tissue and a needle extendable from the probe within a field of view of the ultrasound transducer. The needle may be coupled to a temperature sensor for monitoring a temperature of the target tissue.

Transducer 64 optionally includes a needle guide 66 for insertion of a biopsy needle 68 through the view of the transducer and into the fascia. A thermocouple or other temperature sensing element may then be deployed using the biopsy needle.

Figure 10:
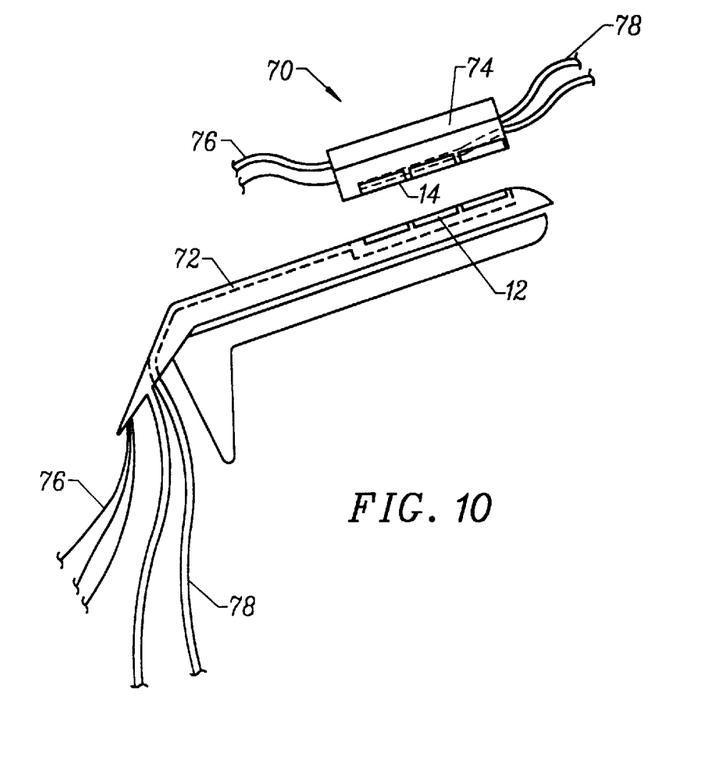
FIG. 10 illustrates an alternative system for selectively shrinking fascia through intermediate tissues, according to the principles of the present invention.

Referring now to FIG. 10, an alternative tissue shrinking system 70 includes an electrode 12 mounted on a speculum 72. Speculum 72 may be used to manually position electrode 12 within the vagina (or another body orifice), while an external applicator 74 is positioned against the skin to clamp the target tissue between electrode 14 and electrode 12. The speculum and external applicator 74 may be manually manipulated to clamp the target tissue between these structures, while electrical leads 76 and cooling fluid conduits 78 couple the probe and applicator to the remaining system components.

Figure 11:
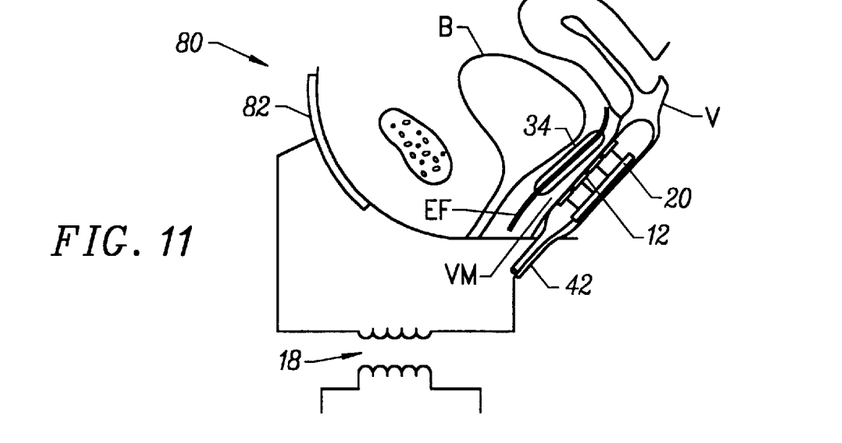
FIG. 11 schematically illustrates an alternative method for selectively shrinking endopelvic fascia using a vaginal probe having a cooled electrode array.

As described above regarding FIG. 2C, the use of bipolar electrodes of differing sizes allows the selective targeting of tissues. Specifically, heating will be concentrated near the smaller electrode surface. By using one electrode surface which is much larger than the other, the current density adjacent the large electrode will remain so low that little tissue heating is produced at that site, so that the very large electrode surface need not be cooled. FIG. 11 schematically illustrates a single probe heating system 80 which takes advantage of this mechanism to selectively heat fascia near a single probe.

In single probe system 80, offset target zone 34 is heated by RF energy selectively directed through the segments of electrode 12. The vaginal mucosa VM disposed between vaginal probe 42 and endopelvic fascia EF is protected by cooling the surface of electrode 12, as described above. Bladder B (and the other tissues opposite endopelvic fascia EF relative to vaginal probe 42) are heated significantly less than endopelvic fascia EF due to the divergence of the current as it travels away from electrode 12 and towards electrode pad 82, which may optionally be disposed on the abdomen, back, or thigh. Optionally, cooling water may be circulated through bladder B to further protect these tissues. Multiplexer 20 selectively energizes the electrode segments for differing amounts of time and/or with differing power to help tailor the temperature profile of offset target zone 34 about endopelvic fascia EF for selective uniform heating with minimal collateral damage. Various treatment regimes with alternating heating and cooling cycles can help to focus the heat therapy on the desired tissues.

Figure 12:
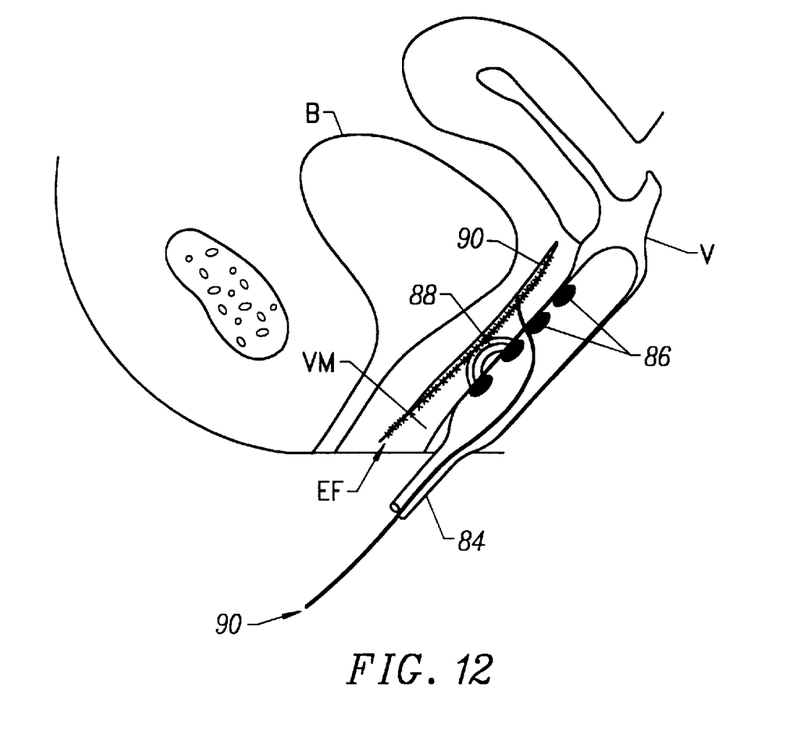
FIG. 12 schematically illustrates a method for selectively shrinking endopelvic fascia by applying a bipolar potential between electrode segments of a vaginal probe, and by electrically insulating a surface of the endopelvic fascia opposite the probe.

Referring now to FIG. 12, a cooled bipolar probe 84 includes many of the structures and features described above, but here includes a series of bipolar electrodes 86. Bipolar electrodes 86 will preferably be cooled, and cooling surfaces may also be disposed between the separated electrodes. As more fully described in co-pending application Ser. No. 08/910,370 bipolar electrodes 86 may optionally be formed as parallel cylindrical structures separated by a predetermined spacing to help direct a bipolar current flux 88 through tissue which lies within a particular treatment distance of probe 84.

The depth of penetration of the bipolar energy is controlled by the spacing and size of the electrode structures. The tissues distant from the cooled electrodes will be heated to a lesser extent than the tissues directly engaged by the electrodes, but will also be cooled to a lesser extent by the cooled electrodes and other cooling surfaces of bipolar probe 84. The tissues close to the electrodes will be heated to a greater extent, and will also be cooled more effectively. Therefore, a controlled regimen of timed pre-cooling and then heating is used to selectively raise the temperature of endopelvic fascia EF (or any other target tissue), while the vaginal mucosa adjacent probe 84 is protected by the cooled probe. Tissues at depths greater than the endopelvic fascia will generally be protected by the dissipation of bipolar current 88. In some embodiments, the electrodes will be separated by a predetermined distance which limits a depth of tissue heating. A depth of the endopelvic fascia and adjacent tissue heated by a bipolar probe can depend on the power applied, on a spacing between the electrodes, and on the surface diameter of the electrodes. An exemplary spacing between the electrodes may be in the range from about 1 to 4 times the electrode diameter, with the electrode diameter often being between about 0.25 mm and 4.0 mm. In some embodiments, a variable spacing between the bipolar electrodes may allow the surgeon to vary the depth of heating.

Since radiofrequency heating generally relies on conduction of electricity through the tissue, one additional mechanism for protecting the tissues at depths greater than the target area would be to inject an insulating fluid 90 into the space surrounding the vaginal wall on the far side of endopelvic fascia EF. Insulating fluid 90 may optionally comprise a gas such as $CO_2$, or may alternatively comprise a liquid such as isotonic Dextran™ in water. Insulating fluid 90 will electrically insulate the adjacent organs and prevent heating of tissues that might otherwise be in contact with the vaginal fascial outer lining. Insulating fluid 90 is here injected using a small needle incorporated into bipolar probe 84, the needle preferably being 22 ga or smaller.

Figure 13:
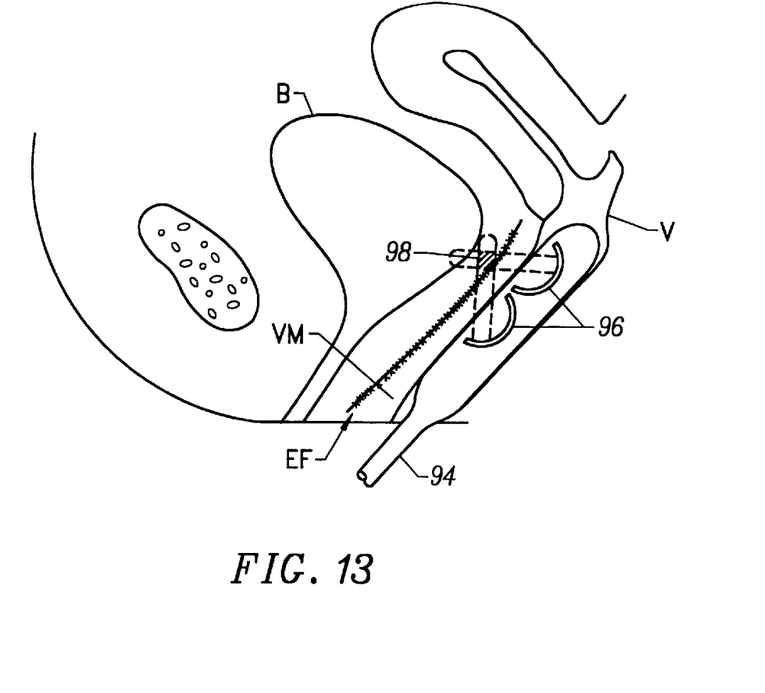
FIG. 13 schematically illustrates a method for selectively shrinking endopelvic fascia by transmitting microwave or ultrasound energy from a cooled vaginal probe.

Referring now to FIG. 13, microwave probe 94 includes microwave antennas 96 which direct microwave heating energy 98 through the vaginal mucosa VM and onto endopelvic fascia EF. Microwave probe 94 will again typically include a cooled probe surface to minimize damage to vaginal mucosa VM. The microwave may optionally be produced by a phased array microwave antenna to decrease heating next to the cold probe relative to the heating of endopelvic fascia EF, or a more conventional microwave antenna may be used.

Microwave power having a frequency of about 2250 MHz is most often used for heating. However, the use of extremely high frequency microwaves would permit constructive interference at the intersection of microwave energy streams by control of the microwave frequency, phase, and electrode spacing. Such constructive interference of microwaves may be used to enhance the heating of the target tissue relative to the heat produced in the intermediate tissue between microwave probe 94 and endopelvic fascia EF (in this example). Injection of an electrically insulating fluid, such as Dextran™, may be used to absorb microwave energy and protect tissues beyond the target zone. In some embodiments, injection of a liquid contrast medium might be used to enhance visualization of the treatment region, increasing the visibility and clarity of the vagina V, bladder B, the other adjacent organs, and the spaces therebetween. Such a contrast medium will typically be highly visible under ultrasonic or fluoroscopic imaging modalities.

An alternative form of energy which may be used in a probe schematically similar to that illustrated in FIG. 13 is ultrasonic heating. A cooled ultrasonic probe could be used to provide heating of the endopelvic fascia adjacent the vagina, preferably while protecting the adjacent tissues using a material which reflects ultrasound. Suitable protection materials include $CO_2$ or a liquid/foam emulsion material. High intensity ultrasound is able to heat tissues at a distance from the probe, and may be focused to apply the most intense heating at a particular treatment site. Concentration of ultrasound energy deep in the body may avoid heating of tissues at the entry site of the focused ultrasound beam, although gas pockets and bony structures may absorb and/or reflect the focused ultrasound energy, so that tissues may be damaged by both localized heating and cavitation. Once again, the surface of an ultrasound probe will typically be cooled to protect the tissues which are directly engaged by the probe.

Figure 14:
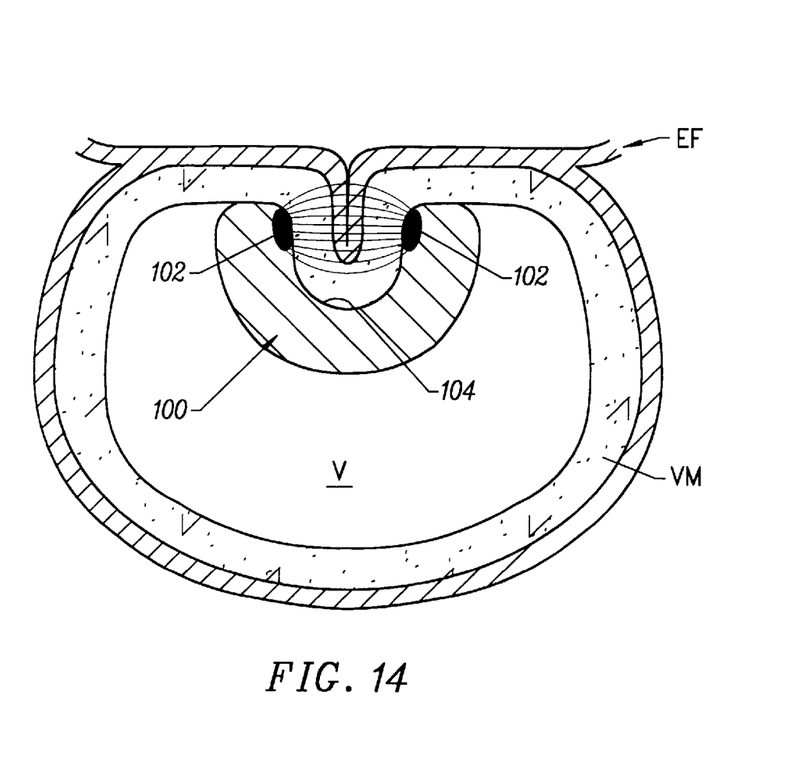
FIG. 14 is a cross-sectional view illustrating a method for selectively shrinking endopelvic fascia by grasping and folding the endopelvic fascia to facilitate focusing of heating upon the fascia, and to enhance shrinkage of the fascia by decreasing tension in the fascia while the fascia is heated, according to the principles of the present invention.

A cross-section of a grasping bipolar probe 100 is illustrated in FIG. 14. Grasping probe 100 grips and folds an anterior portion of the vaginal wall, including both the vaginal mucosa VM and endopelvic fascia EF, as shown. It should be understood that the targeted fascia may be separated from the probe by muscle, vasculature, and the like, as well as by vaginal mucosa VMO. Endopelvic fascia EF is typically about 1 mm thick, while the grasped, folded vaginal wall will typically be between about 10 mm to 14 mm thick. The folded endopelvic fascia EF may thus be heated and contracted between cooled bipolar electrodes 102, as described above. Depending on the length of the fold, cooled bipolar electrodes 102 may optionally be formed as wide elongate plates. Grasping may be accomplished mechanically or by applying a vacuum to draw the vaginal wall into a cavity 104 of grasping probe 100. By drawing the endopelvic fascia into close proximity of both electrodes, a finer focusing of the heating may be accomplished, thereby minimizing the damage to adjacent tissues. Additionally, grasping probe 100 may draw the tissue inward to relieve any tension in the fascia, thereby enhance the shrinkage. As described above regarding FIG. 12, $CO_2$ or some other insulating medium may be used for additional protection of adjacent tissues and organs.

Figure 15:
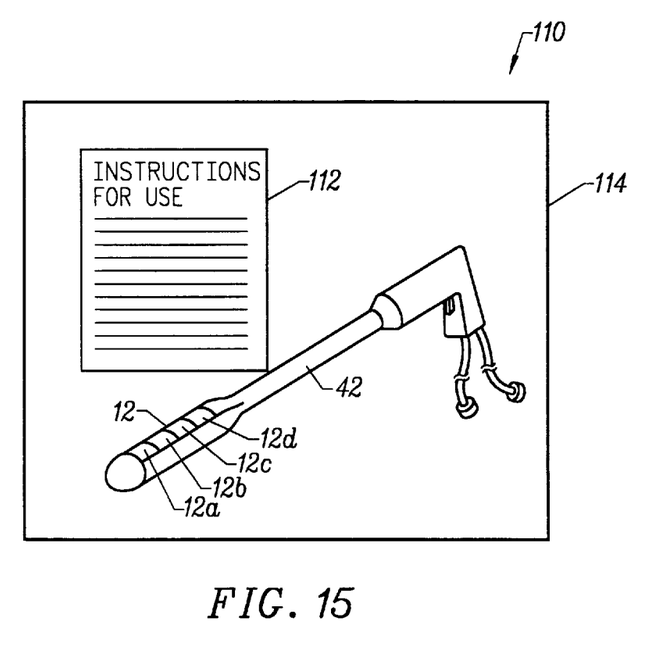
FIG. 15 is a schematic illustration of a kit including the vaginal probe of FIG. 5, together with instructions for its use to shrink tissues, according to the methods of the present invention.

A kit 110 includes vaginal probe 42 and instructions 112 for use of the probe to shrink tissues, the probe and instructions disposed in packaging 114. The instructions may set forth the method steps for using probe 42 described hereinabove for selectively shrinking pelvic support tissues as a therapy for urinary incontinence, or may alternatively recite any of the other described methods. Additional elements for system 10 (see FIG. 1) may also be included in kit 110, or may be packaged separately.

Instructions 112 will often comprise printed material, and may be found in whole or in part on packaging 114. Alternatively, instructions 112 may be in the form of a recording disk or other computer-readable data, a video tape, a sound recording, or the like.

The present invention further encompasses methods for teaching the above-described methods by demonstrating the methods of the present invention on patients, animals, physical or computer models, and the like.

While the exemplary embodiments have been described in some detail, by way of example and for clarity of understanding, a variety of modifications, adaptations, and changes will be obvious to those who skill in the art. For example, substantially coaxial cylindrical electrode surfaces may clamp tubular tissues (such as the cervix) between cooled parallel surfaces for treatment and/or shrinkage. Therefore, the scope of the present invention is limited solely by the appended claims.

What is claimed is:

1. A probe for heating a target tissue of a patient body through an intermediate tissue, the target tissue comprising a collagenous pelvic support tissue, the probe comprising:

a probe body supporting a plurality of electrode surface segments, the electrode surface segments simultaneously engagable against the intermediate tissue, the probe body having a size and configuration suitable for transvaginal insertion, the electrode surface segments oriented for heating the target tissue through a vaginal wall so that the collagenous pelvic support tissue inhibits incontinence;

a cooling system coupled to the probe for cooling the electrode surface segments; and a control system coupled to the electrode surface segments, the control system adapted to selectively energize the electrode surface segments so as to heat the target tissue to a treatment temperature without ablating the target tissue while the cooling system maintains the intermediate tissue disposed between the electrode surface segments and the target tissue below a maximum safe tissue temperature.

2. A probe as claimed in claim 1, further comprising an ultrasound transducer disposable adjacent the intermediate tissue to facilitate aligning the probe with the target tissue.

3. A probe as claimed in claim 2, further comprising a needle extendable from the probe within a field of view of the ultrasound transducer, the needle coupled to a temperature sensor for monitoring a temperature of the target tissue.

4. A probe as claimed in claim 1, wherein the control system is adapted to effect shrinkage of the target tissue, the target tissue comprising a collagenous support tissue.

5. A probe as claimed in claim 4, further comprising a tissue temperature sensor coupled to the control system, the control system limiting a radiofrequency energy applied to the electrode surface segments in response to a tissue temperature signal from the temperature sensor.

6. A probe as claimed in claim 4, wherein the control system limits the energy so that the treatment temperature of the target tissue is in a range from about 60 C to about 110 C while the intermediate tissue engaged by the electrode surface segments remains below about 45 C.

7. A probe as claimed in claim 6, wherein the control system limits a heating time and heating energy so that the target tissue is at the treatment temperature for a time in a range from about 10 seconds to about 2 minutes.

8. A probe as claimed in claim 1, wherein the control system is configured to energize the electrode surface segments after the cooling system precools the intermediate tissue.

9. A probe as claimed in claim 8, wherein the control system is adapted to effect a regimen of timed pre-cooling and then heating.

10. A method for therapeutically heating a target zone of a collagenous support tissue within a female patient body, the method comprising:

engaging a probe against the tissue, the probe having a plurality of electrode surface segments;

cooling the tissue adjacent the probe with the electrode surface segments; and directing an electrical current flux from the electrode surface segments, through the cooled tissue, and into the target zone by selectively energizing the electrode surface segments so that the current flux substantially evenly heats the target zone without ablating the collagenous support tissue, and so that the collagenous support tissue inhibits incontinence, wherein the cooling step inhibits necrosis of the copied tissue during the flux directing step.

11. A method as claimed in claim 10, wherein the flux directing step comprises applying varying electrical potentials to the surface segments, the surface segments defining a substantially flat electrode surface.

12. A method as claimed in claim 10, further comprising monitoring a temperature of the cooled tissue, the target zone separated from the probe by a cooled tissue depth, and limiting the current flux in response to the monitored tissue temperature.

13. A method as claimed in claim 10, wherein the directing energy step comprises applying a bipolar electrical potential between two of the electrode surface segments, the electrode surface segments disposed along a tissue engaging surface of the probe, the cooling step comprising cooling a portion of the tissue engaging surface disposed between the electrode surface segments so that the target zone is separated from the tissue engaging surface by the cooled tissue between the electrode surface segments.

14. A method as claimed in claim 13, further comprising controlling a depth of heating using a spacing between the bipolar electrodes.

15. A method as claimed in claim 10, wherein the cooling step comprises precooling an intermediate tissue engaged by the probe before the current directing step, the intermediate tissue disposed between the probe and the collagenous support tissue.

16. A method as claimed in claim 15, wherein the cooling step further comprises precooling the intermediate tissue for a predetermined time.

17. A probe for heating a target tissue of a patient body through an intermediate tissue, the probe comprising:

a probe body supporting a plurality of electrode surface segments, the electrode surface segments simultaneously engagable against the intermediate tissue;

a cooling system coupled to the probe for cooling the electrode surface segments; and a control system coupled to the electrode surface segments, the control system adapted to selectively energize the electrode surface segments so as to heat the target tissue to a treatment temperature without ablating the target tissue while the cooling system maintains the intermediate tissue disposed between the electrode surface segments and the target tissue below a maximum safe tissue temperature, the control system selectively energizing the segments in response to a depth of the intermediate tissue between the electrode and the target tissue, the energized segments having a smaller area than a total segment area to reduce heating depth in correlation with the intermediate tissue depth.

18. A probe for heating a target tissue of a patient body through an intermediate tissue, the target tissue comprising a fascial sheet, the probe comprising:

a probe body supporting a plurality of electrode surface segments, the electrode surface segments simultaneously engagable against the intermediate tissue, the electrode surface segments disposed along a tissue engaging surface of the probe and the target tissue defining a significant misalignment angle with the tissue engaging surface;

a cooling system coupled to the probe for cooling the electrode surface segments; and a control system coupled to the electrode surface segments, the control system adapted to selectively energize the electrode surface segments so as to heat the target tissue to a treatment temperature without ablating the target tissue while the cooling system maintains the intermediate tissue disposed between the electrode surface segments and the target tissue below a maximum safe tissue temperature, the control system selectively varying an electrical current and heat time from the electrode surface segments in response to the misalignment angle so as to evenly heat the fascial sheet.

19. A probe for heating a target tissue of a patient body through a predetermined intermediate tissue, the probe comprising:

a probe body supporting a plurality of bipolar electrode surface segments, the electrode surface segments simultaneously engagable against the intermediate tissue;

a cooling system coupled to the probe for cooling the electrode surface segments, wherein the cooling system cools the engaged intermediate tissue disposed between the electrode surface segments, the intermediate tissue separating the probe from the target tissue between the electrode surface segments; and a control system coupled to the electrode surface segments, the control system adapted to selectively energize the electrode surface segments so as to heat the target tissue to a treatment temperature without ablating the target tissue while the cooling system maintains the intermediate tissue disposed between the electrode surface segments and the target tissue below a maximum safe tissue temperature, wherein the control system can apply a bipolar electrical potential between electrode surface segments, and wherein the electrode surface segments are adapted to direct a current flux through the engaged intermediate tissue and into the target tissue, the electrode surface segments separated by a spacing determined by a depth of the predetermined intermediate tissue, the electrode spacing controlling a depth of heating of the bipolar energy.

20. A probe as claimed in claim 19, wherein the probe has a size and configuration suitable for transvaginal insertion, and wherein the electrode spacing is suitable for heating the collagenous support tissue through a vaginal wall.

21. A probe as claimed in claim 20, wherein the control system is adapted to effect shrinkage of endopelvic fascia without ablating the endopelvic fascia while the cooling system inhibits necrosis of the vaginal wall.

22. A probe as claimed in claim 19, wherein the controller is adapted to effect a predetermined regimen of precooling and then heating.

23. A method for therapeutically heating a target zone of a collagenous support tissue within a patient body, the method comprising:

inserting a probe transvaginally;

engaging the probe against the tissue, the probe having a plurality of electrode surface segments;

cooling the tissue adjacent the probe with the electrode surface segments, wherein the cooled tissue comprises a vaginal wall; and directing an electrical current flux from the electrode surface segments, through the cooled tissue, and into the target zone by selectively energizing the electrode surface segments so that the current flux substantially evenly heats the target zone without ablating the collagenous support tissue, wherein the cooling step inhibits necrosis of the cooled tissue during the flux directing step, and wherein the current flux directing step heats the collagenous support tissue.

24. A method as claimed in claim 23, wherein the collagenous support tissue comprises endopelvic fascia, wherein the cooling step inhibits necrosis of the vaginal wall, and wherein the flux directing step effects shrinkage of the endopelvic fascia without ablating the endopelvic fascia so as to inhibit incontinence.

25. A method as claimed in claim 22, wherein the flux directing step shrinks the collagenous support tissue.

26. A method as claimed in claim 25, wherein the flux directing step heats the collagenous tissue to a treatment temperature in a range from about 60 C to about 110 C while the cooling step maintains the cooled tissue below about 45 C.

27. A method as claimed in claim 26, wherein the flux directing step heats the collagenous tissue to the treatment temperature for a time in a range from about 10 seconds to 2 minutes.

* * * * *

UNITED STATES PATENT AND TRADEMARK OFFICE
CERTIFICATE OF CORRECTION

PATENT NO.    : 6,081,749
DATED         : June 27, 2000
INVENTOR(S)   : Frank Ingle et al.

It is certified that error appears in the above-identified patent and that said Letters Patent is hereby corrected as shown below:

Drawings,
Fig. 4A, drawing sheet 4 of 8, please delete the term "(PRIOR ART)".
Fig. 4C, drawing sheet 4 of 8, please delete the term "(PRIOR ART)".

Signed and Sealed this

Twenty-eighth Day of January, 2003

JAMES E. ROGAN
*Director of the United States Patent and Trademark Office*